United States Patent [19]
Yurek et al.

[11] Patent Number: 5,690,644
[45] Date of Patent: Nov. 25, 1997

[54] APPARATUS FOR DEPLOYING BODY IMPLANTABLE STENT

[75] Inventors: Matthew T. Yurek, Bloomington; Steven J. Healy, Vadnais Heights, both of Minn.

[73] Assignee: Schneider (USA) Inc., Plymouth, Minn.

[21] Appl. No.: 603,683

[22] Filed: Feb. 20, 1996

Related U.S. Application Data

[63] Continuation of Ser. No. 311,912, Sep. 26, 1994, abandoned, which is a continuation of Ser. No. 998,343, Dec. 30, 1992, abandoned.

[51] Int. Cl.$^6$ .............................. A61F 11/00; A61M 29/00
[52] U.S. Cl. .............................................. 606/108; 606/198
[58] Field of Search ........................... 606/108, 191–198; 604/96–104; 128/657, 772; 623/1, 11, 12

[56] References Cited

U.S. PATENT DOCUMENTS

| | | |
|---|---|---|
| 4,573,470 | 3/1986 | Samson et al. . |
| 4,616,648 | 10/1986 | Simpson . |
| 4,655,771 | 4/1987 | Wallsten . |
| 4,681,110 | 7/1987 | Wiktor . |
| 4,732,152 | 3/1988 | Wallsten et al. . |
| 4,733,665 | 3/1988 | Palmaz . |
| 4,748,982 | 6/1988 | Horzewski et al. . |
| 4,762,129 | 8/1988 | Bonzel . |
| 4,771,777 | 9/1988 | Horzewski et al. . |
| 4,793,348 | 12/1988 | Palmaz . |
| 4,824,435 | 4/1989 | Giesy et al. . |
| 4,848,343 | 7/1989 | Wallsten et al. . |
| 4,877,031 | 10/1989 | Conway . |
| 4,966,138 | 10/1990 | Millar . |
| 4,988,356 | 1/1991 | Crittenden et al. . |
| 5,002,531 | 3/1991 | Bonzel . |
| 5,034,001 | 7/1991 | Garrison et al. . |

(List continued on next page.)

FOREIGN PATENT DOCUMENTS

| | | |
|---|---|---|
| 0321912 | 6/1989 | European Pat. Off. . |
| 0416662 | 3/1991 | European Pat. Off. . |
| 0442657 | 8/1991 | European Pat. Off. . |
| 0505686 | 9/1992 | European Pat. Off. . |
| 0513818 | 11/1992 | European Pat. Off. . |
| WO93/17750 | 9/1993 | WIPO . |

OTHER PUBLICATIONS

PCT Appln. No. WO93/17636 published Sep. 16, 1993 (Jacobson) Search Report in PCT/US93/10978.
Intl. Appln. under PCT Pub. No. WO/93/17750 published Sep. 16, 1993 entitled "Intravascular Catheter and Method for Use Thereof".

*Primary Examiner*—Glenn Dawson
*Attorney, Agent, or Firm*—Haugen and Nikolai, P.A.

[57] ABSTRACT

A stent deployment device includes a flexible, elongate interior catheter and a retaining structure cooperating with the catheter to support a stent along a distal end support region of the catheter. The stent is supported in a reduced radius delivery state to facilitate delivery to a treatment site in a body lumen, by advancing the device over a previously positioned guidewire. An opening at the distal end of the device receives the guidewire into a guidewire lumen of the interior catheter. A second opening through the catheter wall just proximally of the support region allows passage of the guidewire to the exterior of the catheter, whereby the guidewire is contained within the device only along the distal end region. A retainer for the stent can include an exterior catheter surrounding the interior catheter and stent, and moveable axially relative to the interior catheter. A portion of the guidewire proximally of the second opening is contained between the catheters, and can be removed from the exterior catheter through a slit running axially along the exterior catheter. Alternatively, the stent retainer can include a pair of spaced apart sleeves integral with the interior catheter and frictionally retaining opposite ends of the stent, to maintain the stent in the delivery state. In this case the catheter further supports a dilatation balloon surrounded by the stent. The balloon is expanded to free the stent from the sleeves.

31 Claims, 6 Drawing Sheets

U.S. PATENT DOCUMENTS 5,040,548  8/1991  Yock .
5,061,273  10/1991 Yock .
5,102,403  4/1992  Alt .
5,135,535  8/1992  Kramer .
5,180,368  1/1993  Garrison .
5,201,757  4/1993  Heyn et al. .
5,507,768  4/1996  Lau et al. .

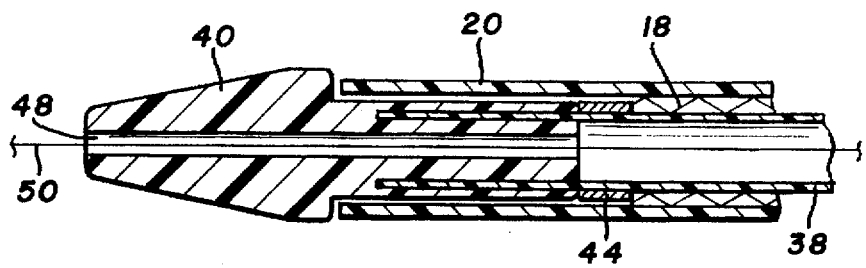
FIG.2
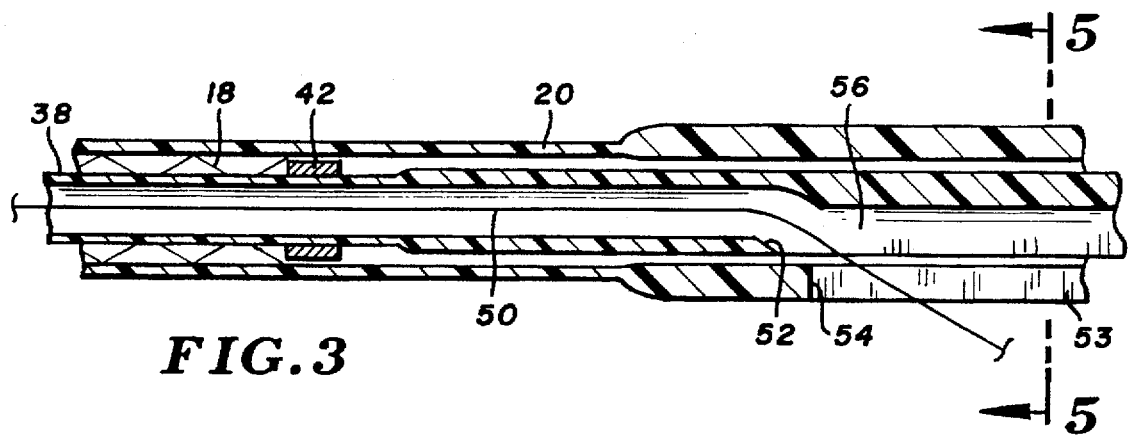
FIG.3
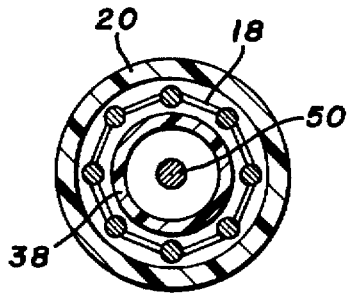
FIG.4
FIG.5

APPARATUS FOR DEPLOYING BODY IMPLANTABLE STENT

This is a continuation of parent application Ser. No. 08/311,912 filed Sep. 26, 1994, which is a continuation of application Ser. No. 07/998,343 filed Dec. 30, 1992, both now abandoned.

BACKGROUND OF THE INVENTION

The present invention relates to devices for deploying body implantable prostheses intended for fixation in body cavities, and more particularly to devices that utilize guidewires in the delivery and placement of stents.

Stents are employed in a variety of patient treatment and diagnostic procedures, for fixation in blood vessels, biliary ducts and other body lumens to maintain the passages. For example, a radially self-expanding stent can be deployed in an artery following a percutaneous transluminal coronary angioplasty (PTCA) procedure or a percutaneous transluminal angioplasty (PTA) procedure. The stent resists a tendency in the vessel to close, thus countering acute reclosure and plaque restenosis. A highly preferred construction for a radially self-expanding stent, disclosed in U.S. Pat. No. 4,655,771 (Wallsten) is a flexible tubular braided structure formed of helically wound thread elements. Wallsten teaches use of a catheter for delivering the stent to the fixation site. A pair of grips maintain the stent at the distal end of the catheter, and are controlled by an operational member at the proximal end of the catheter, to release the stent after positioning and initial medial expansion of the stent.

Another prosthesis construction is disclosed in U.S. Pat. No. 4,681,110 (Wiktor). A flexible tubular liner, constructed of braided strands of a flexible plastic, is delivered into the aorta by a main catheter tube, with the prosthesis carried at the distal end of the main tube. A secondary tube, inside the main catheter tubing and terminating just proximally of the liner, is held in place as the main tube is withdrawn. Thus the liner is deployed initially at its distal end, and radially self-expands against an aneurism to direct blood flow past the aneurism.

Yet another approach to deploying self-expanding stents is shown in U.S. Pat. No. 4,732,152 (Wallsten et al). Often referred to as the "rolling membrane" method, this approach involves a tube or membrane folded over upon itself to provide a double wall for maintaining a self-expanding stent at the distal end of a catheter. The outer wall of the membrane is movable proximally to expose the stent and allow radial self-expansion, beginning at the distal end of the stent.

Prostheses also have been constructed of plastically deformable materials, where upon a dilatation balloon or other means is required to radially expand the stent, e.g. as shown in U.S. Pat. No. 4,733,665 (Palmaz). In Palmaz, a radially expandable vascular graft is delivered by a delivery catheter, with the graft surrounding a dilatation balloon of a balloon catheter. For deployment, the balloon catheter is expanded, thus to expand the graft.

Regardless of the type of prosthesis, its deployment frequently involves guiding the catheter or other delivery appliance through convoluted paths defined by arteries or other body passages. A well known technique for guiding the delivery catheter includes initially positioning a guidewire along the desired path, with the distal end of the guidewire near the treatment site and a proximal portion of the guidewire remaining outside of the body. The delivery catheter is formed with a lumen that runs the length of the catheter. When the proximal end portion of the previously positioned guidewire is threaded into the distal end of the delivery catheter, the delivery catheter can be advanced distally over the guidewire, ultimately to the treatment site for stent deployment.

Procedures that employ guidewires often require exchanging of treatment appliances. For example, a balloon catheter may be employed in a PTA or PTCA procedure, followed by placement of a stent or other prosthesis. This exchange or replacement of catheters requires that the proximal portion of the guidewire protruding from the patient's body be longer than the balloon catheter, the prosthesis delivery catheter, or any other catheter involved in the procedure. This creates difficulty in maneuvering the guidewire and catheters due to the catheter length dimensions involved, which can range from 30 to 300 centimeters. In addition to handling difficulties, the guidewire and catheter tubing generate a substantial frictional force, due to the length along which their respective exterior and interior surfaces interact.

Therefore, it is an object of the present invention to provide a device for delivering and deploying a body implantable prosthesis using a prepositioned guidewire that protrudes from the patient's body a distance substantially less than heretofore required.

Another object is to provide a prosthesis delivery device capable of utilizing a prepositioned guidewire without the need for a guidewire lumen running the entire length of the device.

A further object is to provide a prosthesis deployment device including an outer catheter and a coaxial inner catheter movable axially within the lumen of the outer catheter, in which the inner catheter includes a guidewire receiving lumen only along its distal portion, with a proximal termination open to the exterior of the inner catheter and alignable with an opening through the outer catheter, thus to facilitate passage of the guidewire from the innermost lumen to the exterior of the outer catheter.

Yet another object is to provide a prosthesis delivery device as part of a system of several devices alternatively advanced over a previously positioned guidewire, with exchanges of the devices being substantially simplified due to a shorter guidewire and reduced guidewire/device friction.

SUMMARY OF THE INVENTION

To achieve these and other objects, there is provided an apparatus for deploying a prosthesis at a treatment site within a body lumen. The apparatus includes an elongate prosthesis carrier having a proximal end region and a distal end region including a prosthesis support segment. The carrier has a carrier wall, and a guidewire lumen running axially of the carrier at least along the prosthesis support segment. A first opening is formed at the distal end of the support segment for admitting a guidewire into the guidewire lumen. A second opening through the carrier wall at the proximal end of the support segment provides egress of the guidewire out of the guidewire lumen, whereby the carrier contains the guidewire only along the prosthesis support segment. A prosthesis retaining means releasibly supports a prosthesis in a delivery state along the support segment of the carrier. When in the delivery state, the prosthesis has a reduced radius along its axial length to facilitate delivery of the prosthesis to a treatment site in a body lumen. A control means, operably associated with the retaining means, causes the retaining means to release the prosthesis when the support segment is positioned near the treatment site, thus to facilitate deployment of the prosthesis in a radially expanded state at the treatment site.

One preferred retaining means is a flexible, elongate outer catheter having a catheter lumen for containing the carrier. The outer catheter and carrier are movable relative to each other toward and away from a delivery configuration in which the outer catheter surrounds and radially compresses the prosthesis. Withdrawal of the outer catheter, i.e., proximal movement relative to the carrier, frees the prosthesis for radial expansion. The outer catheter advantageously has a slit running axially from a point near the proximal end of the support segment when the catheter and carrier are in the delivery configuration, to a proximal end region of the outer catheter. This allows the portion of the guidewire proximal to the guidewire lumen to be alternatively positioned within or outside of the outer catheter, as desired.

As compared to a conventional delivery apparatus that receives a guidewire along its entire length, the device of the present invention is substantially easier to manipulate. The proximal or exchange portion of the guidewire that protrudes from a patient's body need not be longer than the entire device, but merely longer than the distal end region. Consequently it is substantially easier for the physician to manipulate a properly positioned guidewire, and easier to position the prosthesis delivery device for advancement along the guidewire. Friction between the guidewire and device occurs only along the distal end region, rather than along the entire length of the device. Typically, the device has a total length up to twenty times the length of the distal end region alone. Thus, static and dynamic frictional forces are substantially reduced, facilitating advancement of the device to the treatment location, particularly over a tortuous path to the desired location.

A preferred carrier is an inner catheter having a distal tip and a radiopaque marker proximally of the distal tip wherein the guidewire lumen is open to the distal tip and extends to the second opening through the wall of the inner catheter. Preferably the second opening is aligned with the distal portion of the slit when the device is in the delivery configuration. A channel or groove can be formed in the inner catheter, beginning at the proximal end of the catheter lumen and extending to the proximal end region of the inner catheter, for containing the portion of the guidewire between the outer catheter and the inner catheter. More preferably, the groove is aligned with the slit along the outer catheter.

The inner catheter with its abbreviated guidewire lumen is advantageous in connection with stents, in a configuration where the stent surrounds the inner catheter, and is surrounded by either the outer catheter, a rolling membrane or the outer catheter in combination with a sleeve extended proximally from the distal tip. In each case, the member or members surround the stent and maintain the stent in its reduced radius state along the prosthesis support segment. In the case of a radially self-expanding stent, stent release is achieved by moving the outer catheter proximally with respect to the inner catheter to free the stent for radial self-expansion.

Conversely, in the case of a plastically expanded stent, it is advantageous to incorporate a dilatation balloon along the inner catheter, particularly along the prosthesis support region. The balloon, surrounded by the stent or other prosthesis, is expandable by a fluid under pressure, provided through a balloon inflation lumen running substantially the entire length of the inner catheter.

Thus in accordance with the present invention, treatment procedures involving deployment of prostheses by means of a previously positioned guidewire are substantially simplified. The physician and others involved in the procedure are freed from the need to accommodate undue lengths of the guidewire and the attendant difficulty in advancing the prosthesis delivery device, and can devote their attention directly to the procedure at hand. The device is readily adapted to deploy either elastically deformable or plastically deformable stents, and can employ a stent retaining sleeve or rolling membrane, or utilize a dilatation balloon to radially expand the stent.

IN THE DRAWINGS

For a further appreciation of the above and other features and advantages, reference is made to the following detailed description and to the accompanying drawings, in which:

FIGS. 2 and 3 are enlarged views of portions of FIG. 1;

FIG. 4 is a sectional view taken along the line 4—4 in FIG. 1;

FIG. 5 is a sectional view taken along the line 5—5 in FIG. 3;

DETAILED DESCRIPTION OF THE PREFERRED EMBODIMENTS

Figure 1:
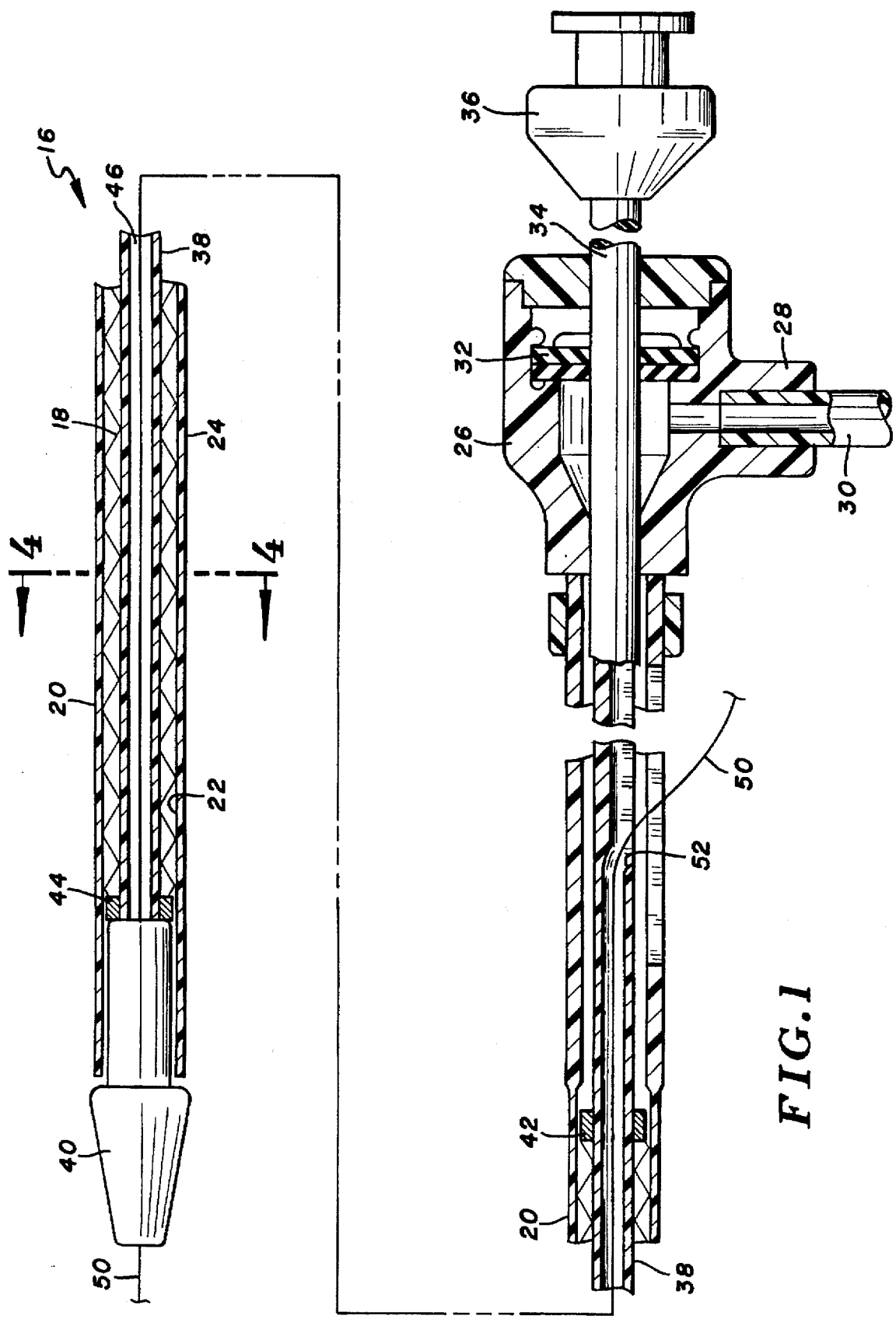
FIG. 1 is a partially sectioned elevation of a device for delivering and deploying a radially self-expanding stent in accordance with the present invention.

Turning now to the drawings, there is shown in FIG. 1 a deployment device 16 for delivering a prosthesis or stent 18 to an intended fixation location within a body lumen, e.g. a blood vessel. After delivering the stent, deployment device 16 is manipulated to controllably release the stent for radial self-expansion to a fixation site within the lumen.

Deployment device 16 includes an elongate and flexible outer catheter or exterior catheter 20 constructed of a biocompatible thermoplastic elastomer, e.g. polyurethane or nylon, typically with an outside diameter in the range of 3–42 Fr. (1–14 mm.). A central lumen 22 runs the length of the exterior catheter. A distal region 24 of the exterior catheter surrounds stent 18, and maintains the stent in a reduced radius and axially elongated delivery configuration, against an elastic restoring force of the stent. Stent 18 when in a normal, unrestrained configuration would have a diameter substantially larger than the interior diameter of lumen 22 (for example, 3–40 mm). Typically the normal or unconstrained stent is larger in diameter than the body lumen in which the stent is fixed, and the restoring force tends to maintain the stent against the tissue wall.

Exterior catheter 20 is mounted at its proximal end to a valve 26. Valve 26 includes a port 28 for receiving a saline solution, radiopaque fluid or the like supplied via an extension tube 30. The fluid proceeds through the valve to central lumen 22. A sealing gasket 32 is mounted in valve 26, and supports an elongate stainless steel tube 34 for axial sliding relative to the valve. Exterior catheter 20 can be pushed and pulled relative to the stainless steel tube by hand manipulation of the valve and a hub 36 at the proximal end of the tube. Stainless steel tube 34 extends distally beyond valve 26 into a proximal portion of lumen 22.

Stainless steel tube 34 is attached to an elongate prosthesis carrier. The prosthesis carrier is embodied as an elongate and flexible inner catheter or interior catheter 38, which can be constructed of the materials similar to those employed to form the exterior catheter. A distal tip 40 is bonded to the distal end of interior catheter 38. Also attached to the interior catheter are a proximal marker 42 and a distal marker 44. The markers are constructed of a radiopaque material, e.g. tantalum or gold, and surround the interior catheter. Markers 42 and 44 are axially spaced apart a distance slightly greater than the axial length of stent 18 when confined in the delivery configuration. The markers identify a prosthesis support segment of the interior catheter, more particularly the distal end region of the catheter, surrounded by stent 18. Markers 42 and 44 have outer diameters slightly smaller than the interior diameter of exterior catheter 20. The stent surrounds interior catheter 38. The coefficient of friction of catheter 20 along its interior surface preferably is less than the coefficient of friction for catheter 38 along its exterior surface. Consequently, when the outer catheter is moved axially relative to the inner catheter, stent 18 tends to remain stationary relative to the inner catheter, rather than traveling with the outer catheter. Catheter 38 thus functions as a carrier for the stent, with catheter 20 providing a prosthesis retaining means for radially compressing the stent and maintaining the stent along the prosthesis support segment, so long as the exterior catheter surrounds the stent.

Interior catheter 38 has a carrier wall that, along the distal end region, defines a guidewire lumen 46 open to the distal end of the interior catheter. An axial passage 48 through distal tip 40 continues lumen 46. A flexible guidewire 50 is contained within lumen 46 and also runs through passage 48.

Stent 18 has an open mesh or weave construction, formed of helically wound and braided strands or filaments of a resilient material, for example a body compatible metal such as stainless steel, a titanium nickel alloy, or a polymer such as polypropylene or polyethylene. As shown in FIG. 1, the stent is elastically deformed, into a reduced radius/increased axial length delivery configuration. The distal region of exterior catheter 20 confines the stent and maintains it in the delivery configuration. When free of catheter 20, stent 18 radially self-expands, i.e. it elastically returns to a normal configuration of increased radius and reduced axial length.

As noted above, hub 36 and stainless steel tube 34 are movable relative to valve 26. More particularly, the valve body is moved proximally relative to the hub, thus to move exterior catheter 20 relative to interior catheter 38. The valve body and hub provide handle means fixed with respect to the proximal ends of the exterior catheter and interior catheter, respectively. The valve body and hub thus cooperate to provide a control means for controllably withdrawing the exterior catheter, relative to the interior catheter, to release stent 18 for radial self-expansion. FIGS. 2 and 3 illustrate a delivery position, in which the distal end of exterior catheter 20 abuts or nearly abuts distal tip 40, surrounding stent 18. As a result, the stent is radially compressed over its entire axial length.

FIG. 3 illustrates the manner in which stent 18 is maintained between exterior catheter 20 and interior catheter 38. As best seen in FIG. 3, lumen 46 does not run the length of interior catheter 38, but rather ends just proximally of proximal marker 42. An aperture 52 through interior catheter 38, open to lumen 46 and to the exterior of catheter 38, allows guidewire 50 to exit catheter 38. An elongate outer catheter opening or axial slit 53, formed through exterior catheter 20, runs axially along the catheter and allows guidewire 50 to exit deployment device 16. When the device (including both catheters) is in the delivery position, aperture 52 of catheter 38 is axially aligned with a distal end 54 of slit 53.

FIG. 5 illustrates catheters 20 and 38 at a region proximally of the prosthesis support segment, where the interior catheter no longer is hollow, and guidewire 50 is outside of the interior catheter. Guidewire 50 runs along side of catheter 38, contained within lumen 22, and includes a proximal portion extended outside of the patient by at least an "exchange" length necessary for inserting and removing device 16 and any other device by means of guidewire 50, while the guidewire remains in position.

Figure 6:
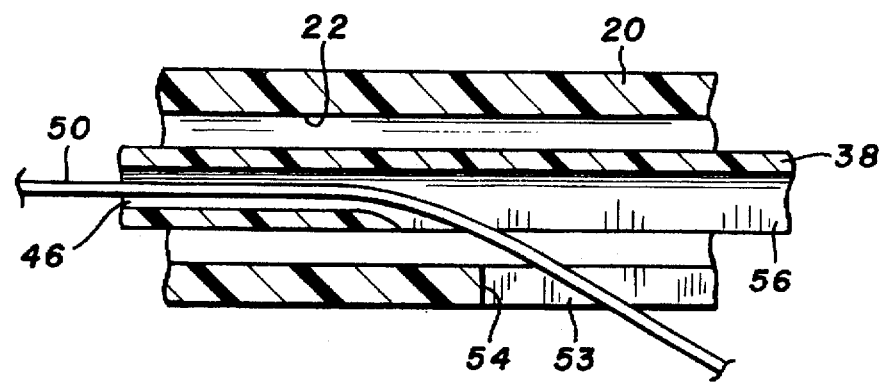
FIG. 6 is sectional view taken along the line 6—6 in FIG. 5.

As seen in FIGS. 5 and 6, a groove 56 is formed axially along interior catheter 38. Groove 56 extends proximally away from the proximal end of guidewire lumen 46, to the proximal end of catheter 38. When guidewire 50 (or any other guidewire) is inserted into lumen 46 via distal tip passage 48 and moved along the lumen, groove 56 provides a guide for channeling the guidewire out of interior catheter 38 through aperture 52.

The portion of the guidewire proximally of guidewire lumen 46 can exit exterior catheter 20 via slot 53. Alternatively, this portion of the guidewire can remain within lumen 22, more particularly within groove 56, over most of the length of device 16. To facilitate moving the guidewire between these alternative positions, slit 53 preferably is angularly aligned with groove 56, i.e., directly adjacent the groove as best seen in FIG. 5. Slit 53 is self-closing due to the residual force or elastic "memory" of catheter 20. At the same time, the exterior catheter readily yields to permit movement of guidewire 50 into and out of the exterior catheter. Groove 56 preferably is slightly larger in width than the guidewire diameter, and extends proximally through stainless steel tube 34.

When deployment device 16 is used to position and fix stent 18, the initial step is to position guidewire 50 with the patient's body. This can be accomplished with a guide cannula (not illustrated), leaving guidewire 50 in place, with the exchange portion of the guidewire extended proximally beyond the point of entry into the patient's body. Deployment device 16 is then advanced over the guidewire at the exchange portion, with the guidewire being received into passage 48 of distal tip 40. As device 16 is inserted into the body, the proximal portion of guidewire 50 travels proximally (relative to the device) to the proximal end of guidewire lumen 46, eventually extending through aperture 52 and emerging from the device through slit 53. At this point, however, this portion of the guidewire is pushed through slit 53, back into lumen 22 and into groove 56 of the interior catheter. The physician or other user continues to advance device 16, while continuing to push the proximal end of the guidewire into exterior catheter 20 through slit 53, until the prosthesis support segment and stent 18 are positioned at the treatment site. At this point, an exchange portion of the guidewire, proximally of slit 53, remains outside of exterior catheter 20.

Figure 7:
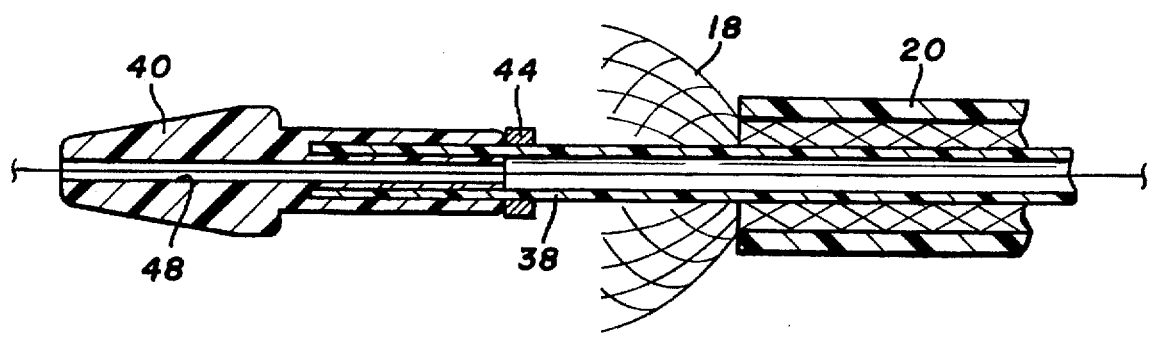
FIG. 7 is a sectioned elevation showing deployment of the stent.
Figure 8:
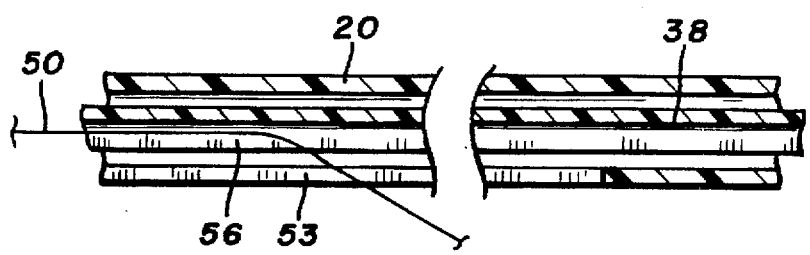
FIG. 8 is a sectional view similar to that in FIG. 3, but with an outer catheter of the device moved proximally relative to an inner catheter of the device.
Figure 9:
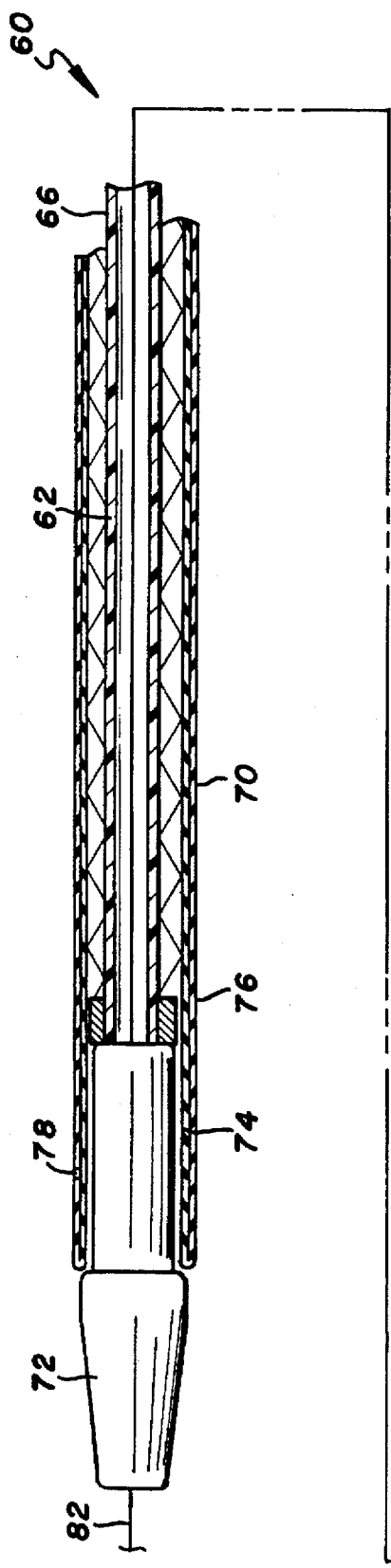
FIG. 9 is a sectioned elevation showing a distal region of an alternative embodiment stent deployment device.
Figure 9:
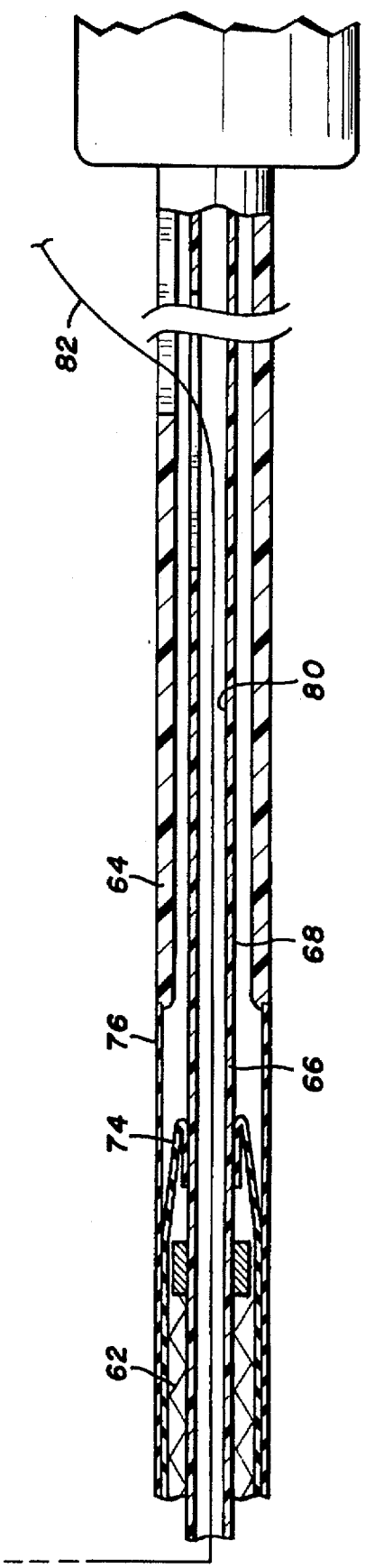
Figure 10:
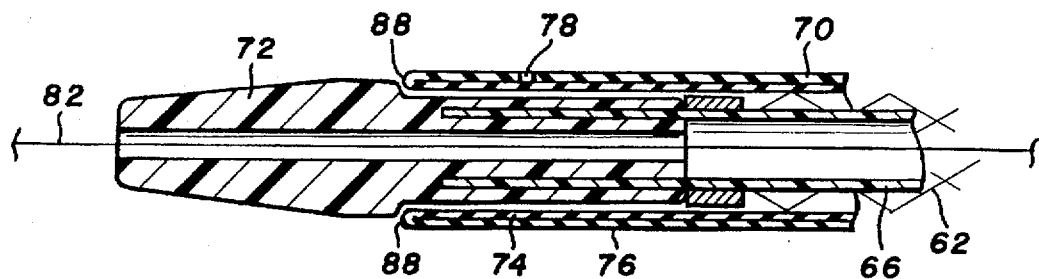
FIG. 10 is an enlarged view of part of FIG. 9.

With device 16 thus positioned, the physician maintains hub 36 and tube 34 substantially fixed with one hand, while moving valve body 26 in the proximal direction with the other hand, thus to move exterior catheter 20 proximally relative to interior catheter 38. As the exterior catheter is retracted, stent 18 remains substantially fixed relative to interior catheter 38, and thus radially self-expands as illustrated in FIG. 7. Continued retraction of the exterior catheter results in complete deployment of the stent. In the fully advanced position, aperture 52 is no longer axially aligned with distal end 54 of the slit, and guidewire 50 runs along groove 56, contained between the catheters as seen in FIG. 8.

After deployment, stent 18 has radially self-expanded to a diameter up to thirty times greater than the diameter of exterior catheter 20. Accordingly, device 16 can be withdrawn proximally through the stent. Guidewire 50 can be withdrawn as well. However, should the medical procedure involve further treatment, e.g., placement of a further stent, the deployment device can be removed without removing the guidewire. This is accomplished by progressively withdrawing device 16 and pulling the device away from the guidewire (which removes the guidewire from within the exterior catheter), all while maintaining the guidewire in place.

Because of slit 53, more particularly the distal end 54 of the slit, guidewire 50 can exit device 16 at a point just proximally of the support segment carrying stent 18, as opposed to exiting the device at the proximal end of catheter 20. As a result, in a device having a length of (for example) 230 centimeters, guidewire 50 can be as short as about 245 centimeters, for an exchange length of about 15 centimeters. By comparison, for a conventional arrangement in which the guidewire emerges from the proximal end of the catheter, the required guidewire length would be over 460 centimeters. Thus, the primary advantage afforded by device 16 is that a substantially shorter guidewire can be employed. Given the much shorter guidewire exchange length afforded by the present invention, device 16 and other apparatus can be threaded onto and advanced along the guidewire with greater ease, and in significantly shorter times. Similarly, devices can be more quickly and conveniently withdrawn while maintaining guidewire 50 in place, since the exchange portion manipulated by the physician or assistant is close to the point of entry into the patient. Insertion and removal are facilitated by the shorter length over which the guidewire and devices are in contact with one another, due to reduced friction between these components. Finally, without the need for a guidewire lumen running the length of interior catheter 38, the interior catheter may be selectively strengthened by a solid structure as indicated.

FIGS. 9–13 illustrate the distal region of an alternative deployment device 60 similar to device 16 in many respects, but illustrating a different approach to confining and deploying a prosthesis such as a radially self-expanding stent 62. Deployment device 60 includes an exterior catheter 64 and an interior catheter 66 within a central lumen 68 of the exterior catheter. Device 60 further includes a valve attached to the exterior catheter, and a hub and stainless steel tube attached to the interior catheter and movable axially relative to the valve. These features are not illustrated, but are substantially identical to the corresponding features of deployment device 16.

Stent 62 is confined in a reduced-radius delivery configuration by a rolling membrane 70 constructed of a suitable body compatible elastomer such as polyurethane. This type of membrane is shown, for example, in U.S. Pat. No. 4,848,343 (Wallsten et al.). Membrane 70 is doubled over upon itself near a distal tip 72, to form an inner layer 74 and an outer layer 76. The membrane is highly pliable and flexible to permit the required distal fold, yet has sufficient elastic strength to overcome the stent restoring force, so long as layers 74 and 76 surround the stent.

Figure 11:
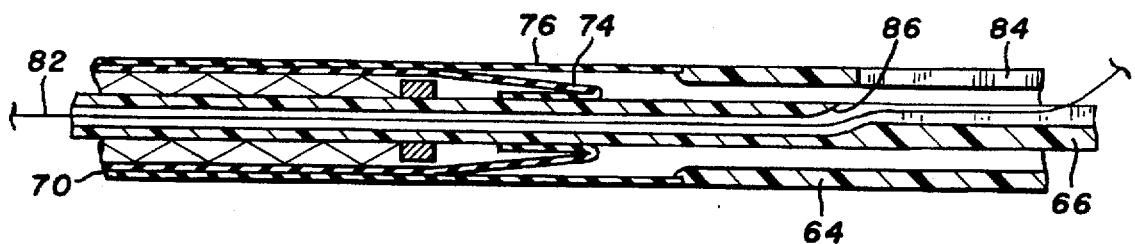
FIG. 11 is an enlarged view of part of FIG. 9.
Figure 12:
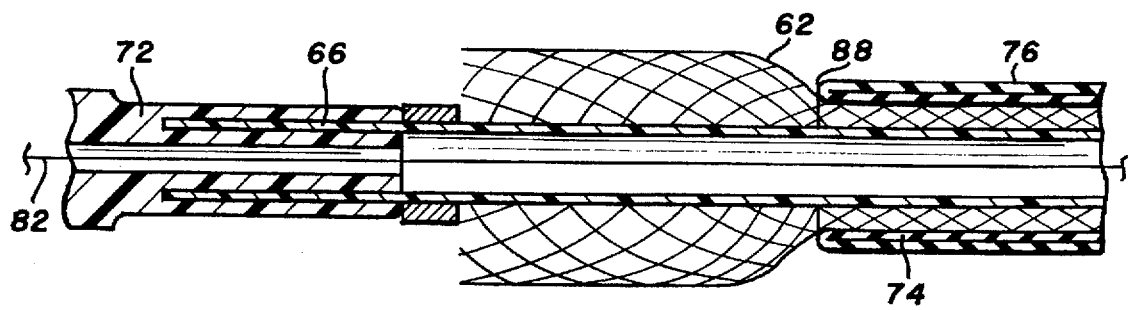
FIG. 12 is a view similar to that of FIG. 10, but with an outer catheter of the device moved proximally relative to an inner catheter of the device.
Figure 13:
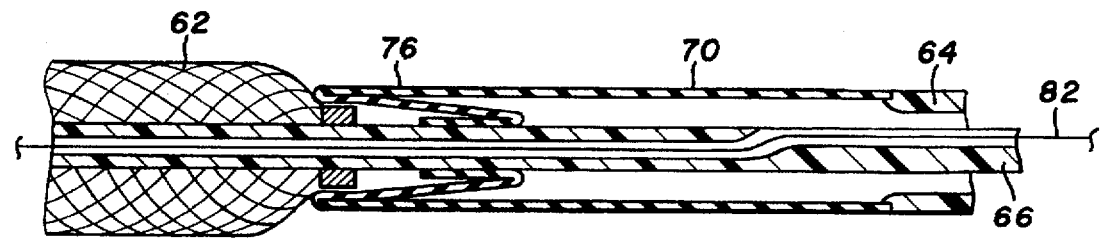
FIG. 13 is a view similar to that in FIG. 11, but with the outer catheter moved proximally relative to the inner catheter.

As seen FIG. 11, outer layer 76 is bonded to the distal end of exterior catheter 64, and the inner fold is similarly bonded to the interior catheter. Thus, fluid (for example a saline solution) supplied under pressure to lumen 68 and outside of interior catheter 66, can flow along membrane 70 between the inner and outer layers. A micropore 78 through outer layer 76 permits the release of trapped air and fluid. A hydrophilic material, for example, polyvinyl pryoladone sold under the brand name Hydromer, is applied to membrane 70 along the outer surface of inner layer 74 and the inner surface of outer layer 76. Silicone or other lubricants also may be employed. The slippery coating facilitates sliding of the inner and outer layers relative to one another.

An inner lumen 80 of interior catheter 66 and a passage through distal tip 72 contain a guidewire 82. The exterior and interior catheters have a slot 84 and an aperture 86 for allowing guidewire 82 to exit device 60 just proximally of the membrane. In the retracted position, i.e. with interior catheter 66 at its most proximal position relative to exterior catheter 64 as shown, the distal end of slot 84 and aperture 86 are axially aligned, and membrane 70 confines the stent.

In general, deployment device 60 is used in the same manner as deployment device 16, in that (1) a guidewire is positioned; (2) the device is loaded onto the exchange portion of the guidewire and advanced to position the stent; and (3) the stent is deployed by pulling the valve and exterior catheter proximally, while holding the stainless steel tube and hub fixed.

Outer layer 76 and a distal fold 88 move proximally with the exterior catheter, thus to "peel" the membrane from around stent 62. This allows the stent to radially self-expand progressively, from its distal end to its proximal end.

With stent 62 fully deployed, device 60 and guidewire 82 may be withdrawn. Alternatively, device 60 may be withdrawn, leaving the guidewire in place, as described in connection with device 16.

Figure 14:
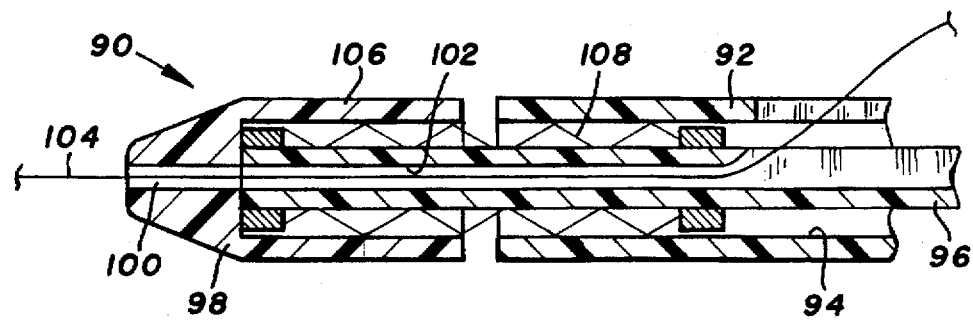
FIG. 14 is a partial side elevation of a further alternative embodiment stent deployment device.

FIG. 14 illustrates the distal region of third embodiment deployment device 90 including an exterior catheter 92 with a central lumen 94, and an interior catheter 96 contained in lumen 94. A distal tip 98 is fixed to the distal end of the interior catheter, and includes a passage 100 that cooperates with a lumen 102 of catheter 96 to accommodate a guidewire 104. A sleeve 106 is integral with tip 98, projects proximally of the tip, and has a diameter substantially equal to the diameter of exterior catheter 92. Sleeve 106 and catheter 92 cooperate to maintain a stent 108 in the reduced radius delivery configuration against its restoring force. Other features of deployment device 90, while not illustrated, are substantially similar to corresponding features of device 16.

Stent 108 is deployed in the same manner as described in connection with device 16, i.e. by pulling the exterior catheter proximally relative to the stationary interior catheter. A critical difference is that stent 108 is deployed first at its medial region, rather than at its distal end. For further information as to medial deployment of stents, and the advantages of medial deployment, reference is made to U.S. patent application Ser. No. 07/863,231, filed Apr. 2, 1992, entitled "MEDIAL REGION DEPLOYMENT OF RADIALLY SELF-EXPANDING STENTS", and assigned to the assignee of the present application.

Figure 15:
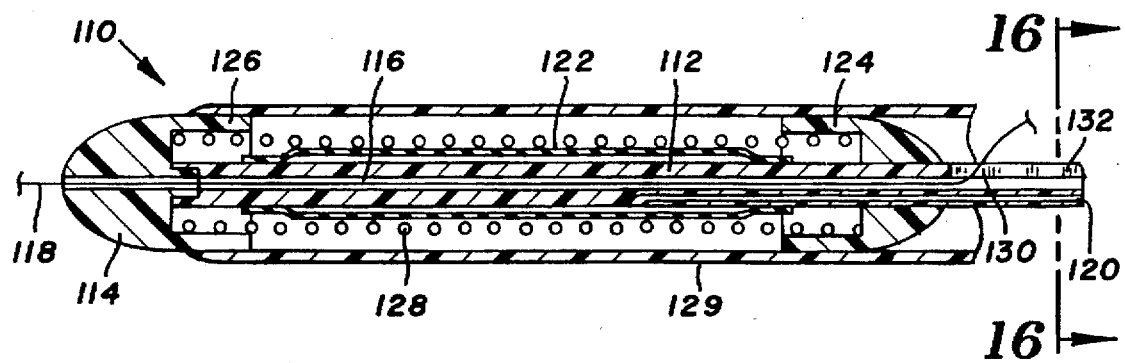
FIG. 15 is a partial side elevation of yet another alternative embodiment stent deployment device.
Figure 16:
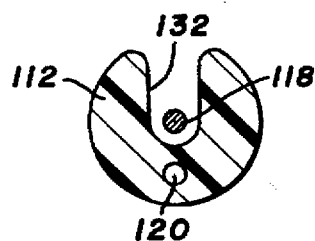
FIG. 16 is a sectional view taken along the lines 16—16 in FIG. 15.

FIG. 15 illustrates the distal region of another deployment device 110 for use with either a radially self-expanding stent, or a plastically deformable stent. Deployment device 110 includes an inner catheter 112 having a distal tip 114, a central lumen 116 for accommodating a guidewire 118, and a balloon inflation lumen 120 open to a dilatation balloon 122 at the distal end portion of the catheter. On opposite sides of the dilatation balloon are proximal and distal sleeves 124 and 126. The sleeves are fixed to catheter 112, and frictionally retain the opposite ends of a self-expanding stent 128, to maintain the stent in a reduced radius delivery configuration. The stent surrounds the dilatation balloon.

As an option, an exterior catheter 129 can be provided, to surround and radially confine stent 128 in the same manner as catheter 20 confines stent 18.

Dilatation balloon 122 is expanded when a fluid, e.g. a saline solution or contrast medium, is supplied under pressure via lumen 120. When outer catheter 129 is employed, this catheter is proximally withdrawn prior to balloon dilatation. As balloon 122 expands, it radially expands stent 128, initially only over a medial region of the stent. Eventually, the stent expansion overcomes the frictional retaining force of sleeves 124 and 126, which frees the stent for radial expansion over its entire axial length, against body tissue represented by broken lines at 131. Preferably, balloon 122 is expandable sufficiently to press stent 128 against tissue 131, at least to a slight degree.

An aperture 130 is provided through the wall of catheter 112, just proximally of proximal sleeve 124. A guide groove 132 similar to that shown in connection with device 16 contains guidewire 118 when the guidewire is within outer catheter 129. The guidewire can be removed to the exterior of outer catheter 129, by virtue of a slit running axially along the outer catheter, much in the same manner as the slits of the other devices.

Figure 17:
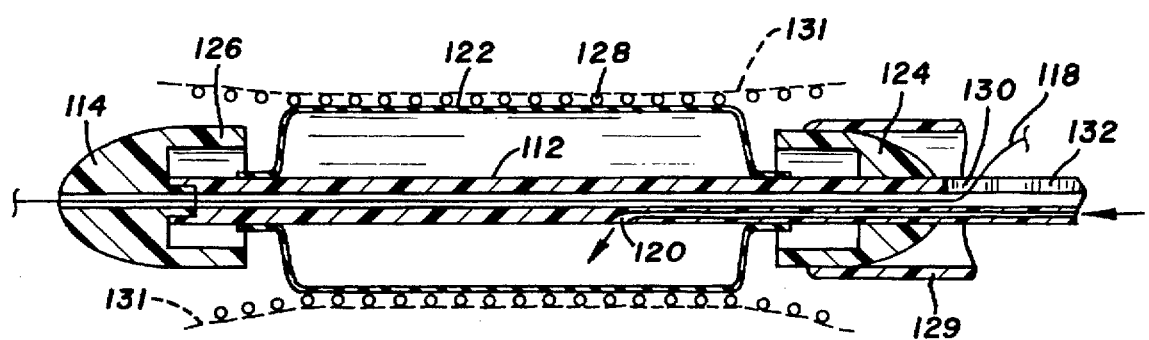
FIG. 17 is a view similar to that of FIG. 15, showing a dilatation balloon of the device in the expanded state.

Deployment device 110 is used in the manner previously described, to deliver and position stent 128. Deployment, however, is accomplished by sliding the outer catheter tube 129 proximally, and then providing a saline solution under pressure to lumen 120, thus to expand dilatation balloon 122. The balloon in its expanded state is shown in FIG. 17. Following a complete stent deployment, device 110 is withdrawn, either while leaving guidewire 118 in place or along with the guidewire. In either event, it is necessary to evacuate balloon 120 before withdrawal, by applying a vacuum to the balloon inflation lumen.

Thus, in accordance with the present invention a prosthesis deployment device is configured to facilitate the use of a guidewire for prosthesis delivery and positioning. The exchange portion of the guidewire is substantially reduced in length, to facilitate loading of the deployment device onto the guidewire. The relatively short distance along with which the device surrounds and contains the guidewire reduces friction to facilitate advancing the device, and further facilitates retraction of the device after prosthesis deployment while leaving the guidewire in place for use in a further procedure. Accordingly, procedures that include deployment of stents or other prostheses can be accomplished more quickly and under improved control, at reduced risk to the patient.

What is claimed is:

1. An apparatus for deploying a prosthesis at a treatment site within a body lumen, in combination with the prosthesis, including:

an elongate prosthesis carrier having a proximal end region, a distal end region having a distal end region axial length, a carrier wall defining a guidewire lumen running axially of the carrier at least along the distal end region, a first opening disposed at a distal end of the distal end region for admitting a guidewire into the guidewire lumen, a second opening through the carrier wall at a proximal end of the distal end region, for providing egress of the guidewire out of the guidewire lumen, and a means for channeling the guidewire out of the guidewire lumen through the second opening whereby the carrier contains the guidewire within the guidewire lumen only along the distal end region;

a prosthesis disposed along the distal end region;

a prosthesis retaining means for releasably supporting the prosthesis in a delivery state along the distal end region, said prosthesis retaining means including a rolling membrane folded over on itself in a delivery configuration whereby said membrane includes an outer fold and an inner fold attached to the prosthesis carrier and surrounded by the outer fold, wherein the membrane when in the delivery configuration is adapted to surround the prosthesis, and wherein the outer fold is movable proximally relative to the carrier away from the delivery configuration and, when so moved, tends to remove the rolling membrane proximally from its surrounding relation to the prosthesis to release the prosthesis, said prosthesis when so supported in the delivery state having a prosthesis length slightly less than the distal end region axial length whereby the prosthesis is between said first and second openings, said prosthesis further having a reduced radius along its axial length to facilitate delivery of the prosthesis to a treatment site in a body lumen; and a control means coupled with respect to the retaining means, for releasing the prosthesis when the distal end region is positioned near the treatment site, thus to facilitate deployment of the prosthesis in a radially expanded state at the treatment site.

2. The apparatus of claim 1 wherein:

the retaining means further comprises a flexible, elongate outer catheter having a catheter wall defining a catheter lumen running axially for substantially the entire length of the outer catheter, the outer catheter having a distal end coupled to the outer fold of said membrane.

3. The apparatus of claim 2 wherein:

the carrier is disposed within the catheter lumen and extends substantially the entire length of the outer catheter, and the outer catheter is movable with respect to the carrier to move the outer fold proximally away from said delivery configuration to release the prosthesis.

4. The apparatus of claim 3 further including:

an outer catheter opening through the catheter wall and disposed near the proximal end of the distal end region when the outer catheter and the carrier are in the delivery configuration.

5. The apparatus of claim 4 wherein:

the outer catheter opening comprises an axial slit extended proximally to a proximal region of the outer catheter.

6. The apparatus of claim 4 wherein:

the carrier comprises an inner catheter having a distal tip, and the first opening is formed through the distal tip.

7. The apparatus of claim 6 wherein:

the outer catheter is moved proximally relative to the inner catheter when moving the membrane away from the delivery configuration to release the prosthesis.

8. The apparatus of claim 7 further including:

a groove in the inner catheter, extended axially from the proximal end of the distal end region to the proximal end region.

9. The apparatus of claim 8 wherein:

the outer catheter opening comprises an axial slit extended proximally to a proximal region of the outer catheter.

10. The apparatus of claim 2 wherein:

the control means further comprises first and second handle means fixed respectively to the proximal end region of the prosthesis carrier and to a proximal end region of the outer catheter, for moving the outer catheter proximally relative to the prosthesis carrier.

11. The apparatus of claim 2 further including:

an axial slit through the catheter wall of the outer catheter, extending from a point near the proximal end of the distal end region when the outer catheter and carrier are in the delivery configuration, to a proximal region of the outer catheter.

12. An apparatus for deploying a prosthesis at a treatment site within a body lumen, in combination with the prosthesis, including:

a flexible, elongate inner catheter having a proximal end region and a distal end region, and further having a catheter wall defining a guidewire lumen open to a distal end of the inner catheter and running axially of the inner catheter at least along said distal end region of the inner catheter, said distal end region having a distal end region axial length;

a prosthesis disposed along the distal end region;

a prosthesis retaining means mounted with respect to the inner catheter and cooperating with the inner catheter to support the prosthesis along the distal end region of the inner catheter and in a delivery state in which the prosthesis has a prosthesis length slightly less than the distal end region axial length, said prosthesis further having a reduced radius along its axial length to facilitate delivery of the prosthesis to a treatment site in a body lumen, said retaining means being operable to release the prosthesis from the delivery state to deploy the prosthesis in a radially expanded state at the treatment site; and a first opening at said distal end of the inner catheter for receiving a flexible guidewire into the guidewire lumen, a second opening through the catheter wall at a proximal end of the distal end region, said second opening allowing passage of the guidewire from within the guidewire lumen to the exterior of the inner catheter, a means for channeling the guidewire out of the guidewire lumen through the second opening whereby the guidewire is contained within the inner catheter substantially only along said distal end region, and a groove in the inner catheter, extending axially from the proximal end of the distal end region to the proximal end region of the inner catheter.

13. The apparatus of claim 12 wherein:

said retaining means comprises first and second sleeves mounted to the inner catheter and adapted for frictionally retaining respective proximal and distal ends of the prosthesis, a dilatation balloon mounted to the inner catheter between the sleeves and surrounded by the prosthesis, and a balloon inflation lumen running substantially the length of the inner catheter for supplying a fluid under pressure to the dilatation balloon.

14. The apparatus of claim 12 wherein:

said retaining means further comprises an outer catheter having an outer catheter lumen running substantially the entire axial length thereof, for containing the inner catheter, the outer catheter being movable relative to the inner catheter toward and away from a delivery configuration in which a distal end region of the outer catheter is adapted to surround the prosthesis and radially compress the prosthesis to maintain the prosthesis in the delivery state.

15. The apparatus of claim 14 further including:

a slit running axially along the outer catheter, from a point near the proximal end of the distal end region when the catheters are in the delivery configuration to a proximal end region of the outer catheter.

16. The apparatus of claim 12 wherein:

the retaining means includes a dilatation balloon at the distal end region and adapted to be surrounded by the prosthesis, and a balloon inflation lumen open to the dilatation balloon and running substantially the length of the inner catheter, for supplying a fluid under pressure to the dilatation balloon to expand the balloon and thereby radially expand the prosthesis when the balloon is so surrounded.

17. The apparatus of claim 12 wherein:

the retaining means includes a flexible and elongate outer catheter having a catheter wall defining a catheter lumen running substantially the length of the outer catheter, wherein the outer catheter, when disposed in a delivery configuration relative to the inner catheter, is adapted to surround the prosthesis.

18. The apparatus of claim 17 wherein:

the inner catheter includes a distal tip, and the outer catheter is adapted to contain the prosthesis within a distal end portion of the catheter lumen and in surrounding relation to the inner catheter adjacent and proximally of the distal tip when the outer catheter and the inner catheter are in the delivery configuration.

19. The apparatus of claim 18 wherein:

the outer catheter surrounds the prosthesis along the entire length of the prosthesis.

20. The apparatus of claim 18 wherein:

the inner catheter further includes a sleeve integral with the distal tip and extending proximally of the distal tip, the sleeve surrounding a distal portion of the prosthesis and the outer catheter surrounding a proximal portion of the prosthesis when the outer catheter and the inner catheter are in the delivery configuration.

21. The apparatus of claim 20 wherein:

the outer catheter abuts the sleeve when the outer catheter and the inner catheter are in the delivery configuration.

22. An apparatus for deploying a prosthesis at a treatment site within a body lumen, in combination with the prosthesis, including:

an elongate prosthesis carrier having a proximal end region, a distal end region having a distal end region axial length, a carrier wall defining a guidewire lumen running axially of the carrier at least along the distal end region, a first opening disposed at a distal end of the distal end region for admitting a guidewire into the guidewire lumen, a second opening through the carrier wall at a proximal end of the distal end region, for providing egress of the guidewire out of the guidewire lumen, and a means for channeling the guidewire out of the guidewire lumen through the second opening whereby the carrier contains the guidewire within the guidewire lumen only along the distal end region;

a prosthesis disposed along the distal end region;

a flexible, elongate outer catheter having a catheter wall defining a catheter lumen running axially for substantially the entire length of the outer catheter, said carrier being disposed within the catheter lumen and extending substantially the entire length of the outer catheter, the carrier and the outer catheter being movable with respect to one another toward and away from a delivery configuration;

a rolling membrane folded over on itself and including an outer fold attached to the outer catheter and an inner fold attached to the carrier, wherein the rolling membrane is adapted to surround the prosthesis when the carrier and the outer catheter are in the delivery configuration, thus to releasably support the prosthesis in a delivery state along the distal end region;

an outer catheter opening through the catheter wall and disposed near the proximal end of the distal end region when the outer catheter and the carrier are in the delivery configuration, to allow passage of the guidewire from within the catheter lumen to the exterior of the outer catheter, said outer catheter opening comprising an axial slit extended proximally to a proximal region of the outer catheter;

said prosthesis when so supported in the delivery state having a reduced radius along its axial length to facilitate delivery of the prosthesis to a treatment site in a body lumen; and a control means coupled with respect to the outer catheter, for moving the outer catheter proximally relative to the carrier away from the delivery configuration to remove the rolling membrane proximally from its surrounding relation to the prosthesis, thereby releasing the prosthesis when the distal end region is positioned near the treatment site, thus to facilitate deployment of the prosthesis in a radially expanded state at the treatment site.

23. The apparatus of claim 22 wherein:

the carrier comprises an inner catheter having a distal tip, and the first opening is formed through the distal tip.

24. The apparatus of claim 23 further including:

a groove in the inner catheter, extending axially from the proximal end of the distal end region, to the proximal end region.

25. The apparatus of claim 23 wherein:

the outer catheter is moved proximally relative to the inner catheter when moving away from the delivery configuration to release the prosthesis.

26. The apparatus of claim 23 wherein:

the control means comprises a dilatation balloon disposed along the distal end region of the carrier and adapted to be surrounded by the prosthesis, and a means for supplying a fluid under pressure to the balloon to expand the balloon and thereby radially expand the prosthesis when the balloon is so surrounded.

27. The apparatus of claim 22 wherein:

the carrier includes a distal tip, and the outer catheter is adapted to contain the prosthesis within a distal end portion of the catheter lumen and in surrounding relation to the carrier adjacent and proximally of the distal tip when the outer catheter and carrier are in the delivery configuration.

28. The apparatus of claim 27 wherein:

the outer catheter surrounds the prosthesis along the entire length of the prosthesis.

29. An apparatus for deploying a prosthesis at a treatment site within a body lumen, in combination with a prosthesis, including:

an elongate prosthesis carrier having a proximal end region, a distal end region having a distal end region axial length, a carrier wall defining a guidewire lumen running axially of the carrier at least along the distal end region, a first opening disposed at a distal end of the distal end region for admitting a guidewire into the guidewire lumen, a second opening through the carrier wall at a proximal end of the distal end region, for providing egress of the guidewire out of the guidewire lumen, a means for channeling the guidewire out of the guidewire lumen through the second opening whereby the carrier contains the guidewire within the guidewire lumen only along the distal end region, and a groove in the prosthesis carrier extending axially from the proximal end of the distal end region to the proximal end region of the prosthesis carrier, said prosthesis carrier having a total length in the range of from 15.3 to about 20 times said distal end region axial length;

a prosthesis disposed along the distal end region;

a prosthesis retaining means for releasably supporting the prosthesis in a delivery state along the distal end region, said prosthesis when so supported in the delivery state having a reduced radius along its axial length to facilitate delivery of the prosthesis to a treatment site in a body lumen; and a control means coupled with respect to the retaining means, for releasing the prosthesis when the distal end region is positioned near the treatment site, thus to facilitate deployment of the prosthesis in a radially expanded state at the treatment site.

30. The apparatus of claim 29 wherein:

the retaining means includes first and second sleeves fixed to the carrier respectively at proximal and distal ends of the distal end region, said sleeves adapted for surrounding and frictionally retaining the prosthesis at respective and opposite ends thereof, to frictionally retain the prosthesis in said delivery state.

31. The apparatus of claim 29 wherein:

said control means includes a dilatation balloon supported at the distal end region and adapted to be surrounded by the prosthesis, and a balloon inflation lumen open to the dilation balloon and running substantially the length of the prosthesis carrier, for supplying a fluid under pressure to the dilatation balloon to expand the balloon and thereby radially expand the prosthesis when the balloon is so surrounded.

* * * * *